United States Patent [19]
Lindström et al.

[11] Patent Number: 5,757,003
[45] Date of Patent: May 26, 1998

[54] METHOD TO DETERMINE THE EXTENT OF OXYGEN PRECIPITATE IN SILICON

[75] Inventors: Lennart Lindström; Tomas Hallberg, both of Linköping, Sweden

[73] Assignee: Forsvarets Forskningsanstalt, Stockholm, Sweden

[21] Appl. No.: 727,563

[22] PCT Filed: Apr. 21, 1995

[86] PCT No.: PCT/SE95/00438

§ 371 Date: Oct. 22, 1996

§ 102(e) Date: Oct. 22, 1996

[87] PCT Pub. No.: WO95/29397

PCT Pub. Date: Nov. 2, 1995

[30] Foreign Application Priority Data

Apr. 22, 1994 [SE] Sweden ................................. 9401386

[51] Int. Cl.$^6$ ................................................ G01N 21/35
[52] U.S. Cl. ................................ 250/341.4; 250/339.08
[58] Field of Search ........................ 250/339.08, 339.12, 250/341.4

[56] References Cited

U.S. PATENT DOCUMENTS

| | | | |
|---|---|---|---|
| 4,429,047 | 1/1984 | Jastrzebski et al. | 436/4 |
| 4,809,196 | 2/1989 | Miller | 364/550.01 |
| 5,066,599 | 11/1991 | Kaneta et al. | 437/7 |
| 5,444,246 | 8/1995 | Kitagawara et al. | 250/341.4 |

FOREIGN PATENT DOCUMENTS 0570100  11/1993  European Pat. Off.

*Primary Examiner*—Don Wong
*Attorney, Agent, or Firm*—Jacobson, Price, Holman & Stern, PLLC

[57] ABSTRACT

The concentration of oxygen clusters in silicon is determined with a spectrometer, for the infrared interval, by obtaining the absorption coefficients for one or more of the wave numbers $728\pm1$, $734\pm1$, $975\pm1$, $988\pm1$, $1000\pm1$, $1006\pm1$ and $1012\pm1$ $cm^{-1}$, using the standard method that is used to determine oxygen atoms in interstitial position and carbon atoms in substitutional position when the measurement is carried out at the wave number 1106 and 605 $cm^{-1}$. The absorption measurements are taken at room temperature and are standardized with respect to the thickness of the sample. The measurements are multiplied with a known calibration constant, whereupon the respective absorption coefficient for the different measured wave numbers are a measure of the concentration of different configurations of the oxygen clusters.

14 Claims, No Drawings

METHOD TO DETERMINE THE EXTENT OF OXYGEN PRECIPITATE IN SILICON

FIELD OF INVENTION

The present invention relates to a method to determine the extent of oxygen clusters in silicon.

BACKGROUND OF THE INVENTION

Crystalline silicon that is used to produce integrated circuits is usually so called Cz-silicon. These silicon crystals are produced according to the Czochralski method and contains relatively high concentrations of oxygen. The presence of oxygen has both advantages and disadvantages. Advantages are a more mechanically stable material and the so called gettering effect, which means that precipitates of oxygen can be used to absorb other undesirable contaminations. Disadvantages are i.a. that areas of different kinds of silicon oxides can develop within the crystals and that electrically active oxygen defects, so called thermal donors, can be created in the temperature range 350°–500° C., a range that is of interest today for producing integrated circuits of very high packaging density.

The oxygen in the Cz-silicon originates from the walls of the quarts container containing the silicon melt and amounts typically to a concentration of $4 \cdot 10^{17} - 1 \cdot 10^{18}$ atoms/cm$^3$. This concentration corresponds to the solubility of oxygen atoms in melted silicon. At lower temperatures the solubility is lower and the supersaturation of oxygen that will therefore occur results in local clusters of silicon-oxygen compounds, $Si_xO_y$, where different values of x and y are conceivable. These clusters have other electrical properties than silicon and can therefore disturb the functioning of a IC-circuit. The development towards smaller and smaller active elements in the silicon technology means that these clusters are able to affect the function and yield of circuit manufacturing more and more.

In spite of the fact that the thermal donors created during heat treatment processes in the range 350°–500° C. have been studied since the middle of the 1950's, no method exists up to now that directly measures the content of the silicon-oxygen complexes that are the underlying cause.

SUMMARY OF THE INVENTION

The present invention solves this problem and gives an image of the extent of micro clusters and in which configurations they exist by being designed in the way that measures the absorption coefficients for one or more specific wave numbers using the standard spectrometer method for the infrared interval known for determining oxygen atoms in interstitial position and carbon atoms in substitutional position. In the known standard method, the absorption coefficient measurement for the oxygen atoms and the carbon atoms is carried out at the wave numbers 1106 and 605 cm$^{-1}$, respectively, and the absorption measurements are carried out at room temperature, standardizing the measurement results with respect to the thickness of the sample and multiplying the results with a known calibration constant. However, in the present invention, one or more different wave numbers are used in the standard method to determine for the first time the extent of oxygen clusters in the silicon. The wave numbers discovered according to the present invention for measuring the absorption coefficients are one or more of the wave numbers 728±1, 734±1, 740±1, 795±1, 988±1, 1000±1, 1006±1 and 1012±1 cm$^{-1}$. The method according to the invention is an important complement to the standard methods existing today to determine the concentrations of individual oxygen and carbon atoms in silicon and are based on knowledge from optical and electrical measurements, by which a correlation between vibrational absorption of oxygen atoms and different electrically active centres have been established. The measurement is carried out at room temperature in a spectrometer for the infra-red interval and means that the intensity of the absorption bands corresponding to the wave numbers 728±1, 734±1, 740±1, 975±1, 988±1, 1000±1, 1006±1 and 1012±1 cm$^{-1}$ are measured and standardized for the thickness of the sample.

DESCRIPTION OF THE PREFERRED EMBODIMENTS

From a technical point of view, the method of measurement is identical to the one used as a standard method for determining the oxygen and carbon content in silicon, when the intensity of two absorption bands corresponding to the wave numbers 1106 and 605 cm$^{-1}$ are measured, whereupon a correction is made for the thickness of the samples and a multiplication with known calibration constants. The known method measures the content of oxygen atoms in an interstitial position and carbon atoms in a substitutional position. Oxygen and carbon atoms in other positions are not detected with this method.

The difference in comparison to the known method is in principle that one measures at different wave numbers. The absorption coefficient is a direct measure of the number of oxygen atoms and can be used to determine the number of thermal donors.

The absorption peak at the respective wave numbers corresponds to oxygen clusters of a certain configuration. By measuring at several wave numbers it is possible to get an image of the extent of oxygen clusters and of the distribution between different types of oxygen clusters.

At the calculations it is possible to use the same calibration constant as is used in determining interstitial oxygen. In the continued development of the method it is possible that improved values can be achieved with a slightly adjusted calibration constant. The calibration constant for oxygen gives, however, a good estimation of the content and distribution of different types of oxygen clusters.

The measurements can be carried out with different kinds of spectrometers for the infra-red interval. A modern Fourier Transform Infra-Red spectrometer, FTIR, is very suitable in this connection.

We claim:

1. A method for determining the concentration of oxygen clusters in silicon using a standard method for measuring the concentration of interstitial oxygen and substitutional carbon in silicon, said standard method comprising measuring the absorption coefficients at the wave numbers 1106 and 605 cm$^{-1}$, respectively, with a spectrometer for the infrared interval, at room temperature, standardizing the measurements with respect to the thickness of the sample, and multiplying them with a predetermined calibration constant, said method for measuring the concentration of oxygen clusters in silicon comprising:

measuring the absorption coefficient at one or more of the wave numbers, 728±1, 734±1, 740±1, 975±1, 988±1, 1000±1, 1006±1 and 1012±1 cm$^{-1}$; said absorption coefficients measured at different wave numbers being a measure of the concentration of different configurations of oxygen clusters.

2. The method of claim 1, further comprising selecting a calibration constant which is the same calibration constant that is used in determining the interstitial oxygen.

3. The method of claim 1, further comprising measuring said absorption coefficients with a Fourier Transform Infra-Red spectrometer.

4. A method for determining the concentration of oxygen clusters in silicon, which method comprises the steps of:
   (a) obtaining a silicon sample for measuring, said sample having a known thickness;
   (b) measuring, with a spectrometer for the infrared interval, the absorption coefficients of said sample for one or more wave numbers selected from the group consisting of 728±1, 734±1, 740±1, 975±1, 988±1, 1000±1, 1006±1 and 1012±1 $cm^{-1}$, said measurements being taken at room temperature;
   (c) standardizing the measurements obtained in step (b) with respect to the thickness of the sample measured; and
   (d) multiplying the standardized measurements with a predetermined calibration constant, said respective absorption coefficient for the different measured wave numbers being a measure of the concentration of different configurations of oxygen clusters.

5. A method according to claim 4, further comprising selecting calibration constants used in determining interstitial oxygen.

6. A method according to claim 4 further comprising making measurements with a Fourier Transform Infra-Red spectrometer.

7. The method of claim 4, wherein the wave number is 1012±1 $cm^{-1}$.

8. The method of claim 4, wherein the wave number is 1006±1 $cm^{-1}$.

9. The method of claim 4, wherein the wave number is 1000±1 $cm^{-1}$.

10. The method of claim 4, wherein the wave number is 728±1 $cm^{-1}$.

11. The method of claim 4, wherein the wave number is 734±1 $cm^{-1}$.

12. The method of claim 4, wherein the wave number is 740±1 $cm^{-1}$.

13. The method of claim 4, wherein the wave number is 975±1 $cm^{-1}$.

14. The method of claim 4, wherein the wave number is 988±1 $cm^{-1}$.

* * * * *

UNITED STATES PATENT AND TRADEMARK OFFICE
CERTIFICATE OF CORRECTION

PATENT NO. : 5,757,003
DATED : May 26, 1998
INVENTOR(S) : Lennart Lindstrom et al.

It is certified that error appears in the above-identified patent and that said Letters Patent is hereby corrected as shown below:

Column 1, line 65, cancel "795+1" and insert --975+1--.

Signed and Sealed this

Twenty-ninth Day of September, 1998

Attest:

BRUCE LEHMAN

Attesting Officer

Commissioner of Patents and Trademarks